US006413207B1

(12) United States Patent
Minami

(10) Patent No.: US 6,413,207 B1
(45) Date of Patent: Jul. 2, 2002

(54) ELECTRONIC ENDOSCOPE APPARATUS

(75) Inventor: Itsuji Minami, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/666,183

(22) Filed: Sep. 21, 2000

(30) Foreign Application Priority Data

Sep. 30, 1999 (JP) .......................................... 11-278571

(51) Int. Cl.[7] ................................................. A61B 1/05
(52) U.S. Cl. ....................... 600/109; 600/160; 600/168; 600/179; 348/68; 348/69; 348/221
(58) Field of Search ................................ 600/109, 160, 600/168, 179, 180, 178; 348/68, 69, 220, 221

(56) References Cited

U.S. PATENT DOCUMENTS

| 4,646,724 A | * | 3/1987 | Sato et al. .................. 600/109 |
| 5,096,292 A | * | 3/1992 | Sakamoto et al. ........ 356/241.1 |

FOREIGN PATENT DOCUMENTS

JP          04-233874     *   8/1992   .......... H04N/5/232

* cited by examiner

*Primary Examiner*—John Mulcahy
(74) *Attorney, Agent, or Firm*—Snider & Associates; Ronald R. Snider

(57) ABSTRACT

The present application relates to an electronic endoscope apparatus for forming a preferable static image by controlling blurring of an image at the time of picking up the image by using a variable-power mechanism. This endoscope emits stroboscopic light by a stroboscopic light emission circuit when a freeze button is pressed and sets a high shutter speed shorter than an exposure time for a dynamic image by an electronic shutter circuit. Moreover, observation distances can be changed by moving a movable lens through a variable-power motor section and a linear transmission member in accordance with operation of a variable-power switch. Therefore, a static image is formed trough short-time image pickup by strong illumination light and image blurring is eliminated which becomes remarkable in particular when the image is enlarged through variable-power operation.

3 Claims, 3 Drawing Sheets

ELECTRONIC ENDOSCOPE APPARATUS

BACKGROUND OF THE INVENTION

1. Field of the Invention

The present invention relates to an electronic endoscope apparatus, particularly to a configuration for forming a static image by using a stroboscopic light-emitting mechanism in an apparatus capable of enlarging an observation image by an optical variable-power (magnification) function or the like.

2. Description of the Prior Art

For a recent endoscope, it is proposed to set a variable-power driving mechanism for changing observation distances (varifocal optical system) or focal distances (zoom optical system) to an insertion front end in order to enlarge an observation object picked up by illumination light and drive a movable lens which is a component of the variable-power mechanism. In this case, the torque of a motor is transmitted to a variable-power mechanism by using a linear transmission member such as a multiple-coil-spring member where rotational motion is converted into linear motion to move a predetermined movable lens of an objective optical system forward or backward and execute variable-power operation. Thereby, it is possible to observe an observation object by enlarging it and perform fine diagnosis.

BRIEF SUMMARY OF THE INVENTION

Object of the Invention

However, though the electronic endoscope apparatus having the variable-power function makes it possible to observe a detailed image of a lesion or the like by enlarging the inside of an observation object by a monitor or the like, there is a problem that the observation object may be blurred. That is, enlarging an observation object represents that blurring due to the pulsation of an observation portion or blurring due to movement of the front end of an endoscope when inserted appears as a large blurring (enlarged and emphasized) even if it is small under standard observation. Particularly when forming and recording a static image, the blurring cannot be ignored.

To decrease the blurring of an observation image, it is considered to raise an electronic shutter speed by controlling the charge storing time of a solid-state image pickup device. However, when increasing the electronic shutter speed while enlarging an observation image, illumination irregularity occurs because the distance between the endoscope front end and the observation object decreases in the case of a varifocal optical system. In the case of a zoom optical system, on the other hand, because the distance between the endoscope front end and the observation object is constant, sufficient illumination light is not applied to the observation object and thereby, exposure deficiency occurs.

The present invention is made to solve the above problems and its object is to provide an electronic endoscope apparatus capable of controlling blurring of an image and forming a preferable static image when picking up an image by using a variable-power mechanism.

SUMMARY OF THE INVENTION

To attain the above object, an endoscope apparatus of the present invention includes a solid-state image pickup device for picking up an observation object, an electronic shutter circuit for controlling the charge storing time of the solid-state image pickup device, a stroboscopic light-emitting section for instantaneously emitting stroboscopic light stronger than the illumination light applied to an observation object under normal observation, and a control circuit for setting a shutter speed faster than a shutter speed for a dynamic image by the electronic shutter circuit when a static image is selected by a freeze signal and controlling the stroboscopic light-emitting section so as to emit stroboscopic light.

Moreover, in the case of another aspect of the present invention, an optical variable-power mechanism capable of optically enlarging an observation image by an objective optical system is included and the above control circuit increases the above shutter speed and emits stroboscopic light when a static image is selected while this optical variable-power mechanism is operated.

By setting not only a static-image-forming light source but also a light source used to form a dynamic image to the stroboscopic light-emitting section, it is possible to additionally turn on the static-image-forming light source when the control circuit receives a freeze operation signal. Moreover, it is permitted to set an LED to the front end of an electronic endoscope as the above static-image-forming light source.

According to the above aspect of the present invention, when a freeze button is pressed, a high shutter speed in which exposure time is shorter than that for a dynamic image is set and stroboscopic light is emitted. The stroboscopic light is obtained by instantaneously turning on a light-source lamp at a high voltage or turning on a lamp or an LED added to a stroboscope together with a normal lamp. Thereby, short-time image pickup is realized without causing illumination irregularity or exposure deficiency and it is possible to obtain a clear static image.

According to the above another aspect of the present invention, by driving, for example, a movable lens of an optical variable-power mechanism, it is possible to obtain an observation distance from a wide angle end (Far) up to an enlargement (Near) end and an image in which an observation object is enlarged. Moreover, when a freeze button is pressed and a shutter speed (exposure time) is set to approx. 1/60 sec in the standard state in the case of the above shutter speed control, the shutter speed is set so as to be raised as an enlargement rate rises from 1/500 sec, 1/1,000 sec and . . . while a variable-power function operates and at the same time, stroboscopic light is output. Thereby, because blurring which becomes remarkable in an enlarged static image is controlled, it is possible to obtain an enlarged static image having a preferable quality.

DETAILED DESCRIPTION OF THE PREFERRED EMBODIMENT

Figure 1:
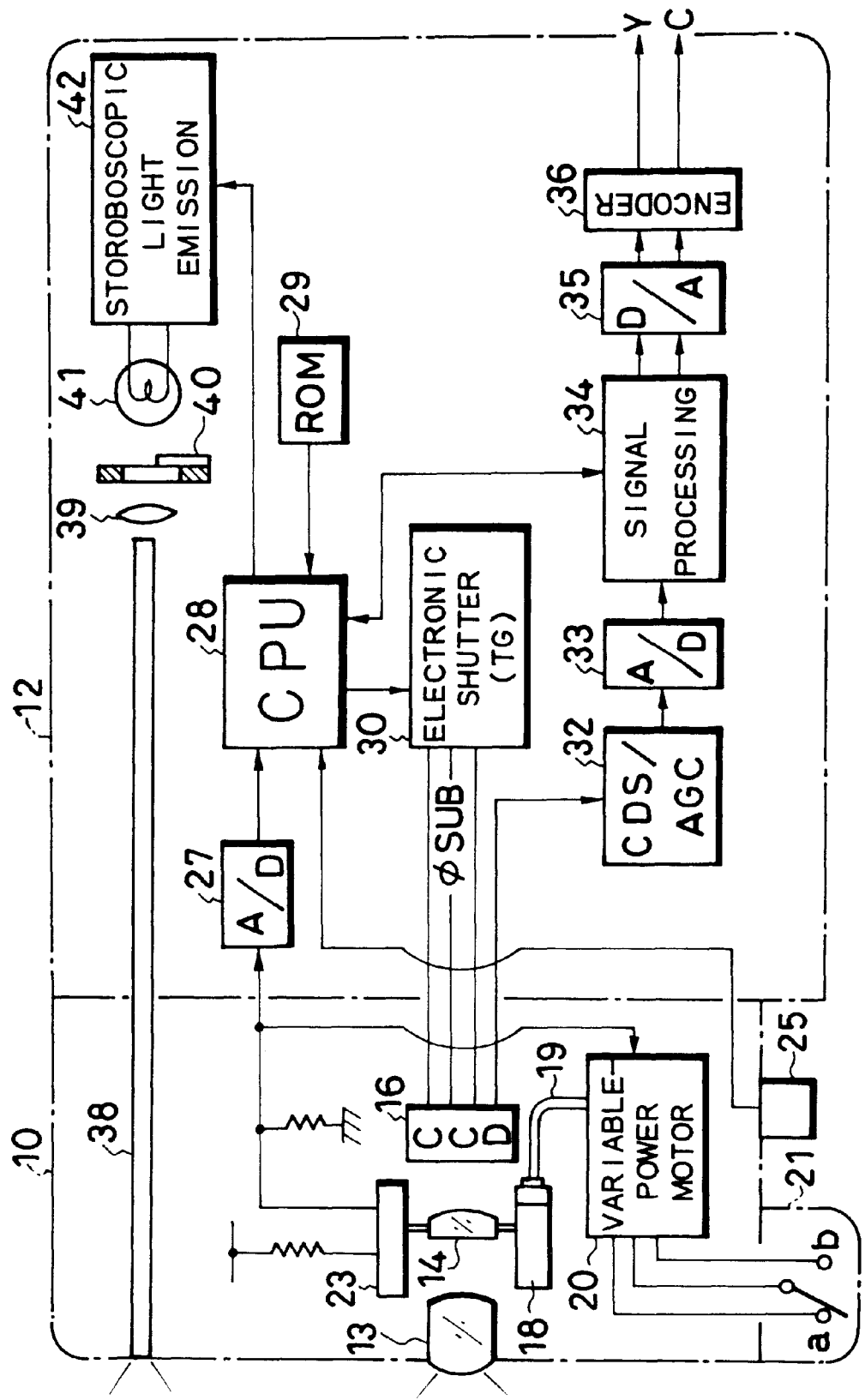
FIG. 1 is a block diagram showing a general configuration of an electronic endoscope apparatus of an embodiment of the present invention.

FIG. 1 shows a configuration of an electronic endoscope apparatus of an embodiment. The electronic endoscope (scope) 10 in FIG. 1 is connected to a processor unit 12 by a connector. The electronic endoscope 10 is provided with a front lens 13 and a movable lens 14 to be moved forward and backward as a varifocal objective optical system for changing observation distances and a zoom objective optical system allowing focal distances to be changed and a CCD 16 for receiving the image light of an observation object is set behind the movable lens 14.

The movable lens 14 is driven by an optical variable-power driving mechanism (details of the mechanism are disclosed in U.S. patent application Ser. No. 09/526,874) comprising a lens moving mechanism section 18, a linear transmission member 19, and a variable-power motor section 20. To convert rotational motion into linear motion, the lens moving mechanism section 18 is, for example, configured so as to provide a female-screw portion for the holding member of the movable lens 14, screw the male-screw portion of a rotational driving body to the female-screw portion, and connect the linear transmission member 19 to the rotational driving body.

The linear transmission member 19 uses a multiple-coil-spring member or the like and is connected to a driving motor in the variable-power motor section 20. Therefore, according to the optical variable-power driving mechanism, the linear transmission member 19 is rotated in accordance with the rotation of the motor and the rotation of the member 19 is converted into linear motion due to connection between the rotational driving body and a lens holding member. As a result, the movable lens 14 moves forward and backward and thereby, variable-power operation is performed. It is possible to substitute the driving means of the movable lens 14 by other actuator.

In the case of this embodiment, an observation distance (focal distance) is set to the wide-angle (contraction) direction by moving the movable lens 14 forward and set to the enlargement direction by moving the lens 14 backward. Moreover, a variable-power switch (such as a seesaw switch) 21 for operating the variable power (or zoom) is set to an operating section or the like. For example, enlargement-directional operation is performed by connecting the lens 14 to a terminal "a" of the variable-power switch 21 and wide-angle-directional operation is performed by connecting the lens 14 to a terminal "b" of the switch 21. Moreover, it is possible to change moving speeds in accordance with a pressed distance of the switch 21.

Moreover, an encoder 23 is set to the upper holding member of the movable lens 14 and a variable-power position (driving position) of the movable lens 14 is detected by the encoder 23. An output of the encoder 23 is supplied to the variable-power motor 20 and position control is performed in accordance with the current detected position and a target variable-power position. Moreover, a freeze button 25 for forming and recording a static image is set to the operating section of the electronic endoscope 10.

On the other hand, a CPU 28 for generally controlling circuits and an electronic shutter circuit 30 are set to a light source and the processor unit 12. The CPU 28 receives an operation signal of the freeze button 25, controls a static image, and controls the stroboscopic light emission to be mentioned later. An output of the encoder 23 for confirming the enlargement position of the variable-power operation is input to the CPU 28 through an A/D (analog/digital) converter 27 and connects with a ROM 29. The ROM 29 stores a control pattern (table) data of an electronic shutter speed to be accelerated in accordance with an enlargement rate or an electronic shutter speed to be accelerated when a static image is selected.

The electronic shutter circuit 30 includes a timing generator (TG) to control an electronic shutter in accordance with a driving signal for driving the CCD 16. When the freeze button 25 is operated or the variable-power switch 21 is operated, the circuit 30 executes acceleration control of the electronic shutter by receiving a command signal from the CPU 28. That is, a shutter speed higher than that when the variable-power mechanism is not operated is set by adjusting the sweep-out time in the charge storing operation of the CCD 16 and changing charge storing times (exposure times). It is possible to control image blurring which becomes remarkable when an image is enlarged in accordance with the electronic shutter speed control.

On the other hand, to video-process a video signal obtained by the CCD 16, the following are used: a CDS (Correlated Double Sampling)/AGC (Automatic Gain Control) circuit 32 for performing clamping and signal amplification, an A/D converter 33, a signal processing circuit 34 for forming, for example, a color-difference signal C and a brightness signal Y and performing various processings such as gamma compensation and contour compensation, a D/A converter 35, and an encoder 36 for performing output processing to a monitor.

A light guide 38 is extended from the electronic endoscope 10 up to the light source and the light-source section of the processor unit 12, a diaphragm 40 is set to the light incoming end of the light guide 38 through a condenser lens 39, and a light-source lamp 41 is set behind the diaphragm 40. The diaphragm 40 is driven by a not-illustrated diaphragm driving circuit and it is possible to adjust the output quantity of light of the diaphragm 40 by changing the opening degree of the diaphragm 40 and keep the brightness of an image constant.

A stroboscopic light emission circuit 42 for normally turning on/off the lamp 41 and for controlling stroboscopic light emission is connected to the light-source lamp 41. The stroboscopic light emission circuit 42 outputs a normal turn-on voltage when a dynamic image is formed and supplies a turn-on voltage instantaneously rising up to a voltage higher than the above normal voltage for a predetermined period (period equal to or more than one vertical-operation period) when the freeze button 25 is pressed to make the lamp 41 emit stroboscopic light.

Figure 2:
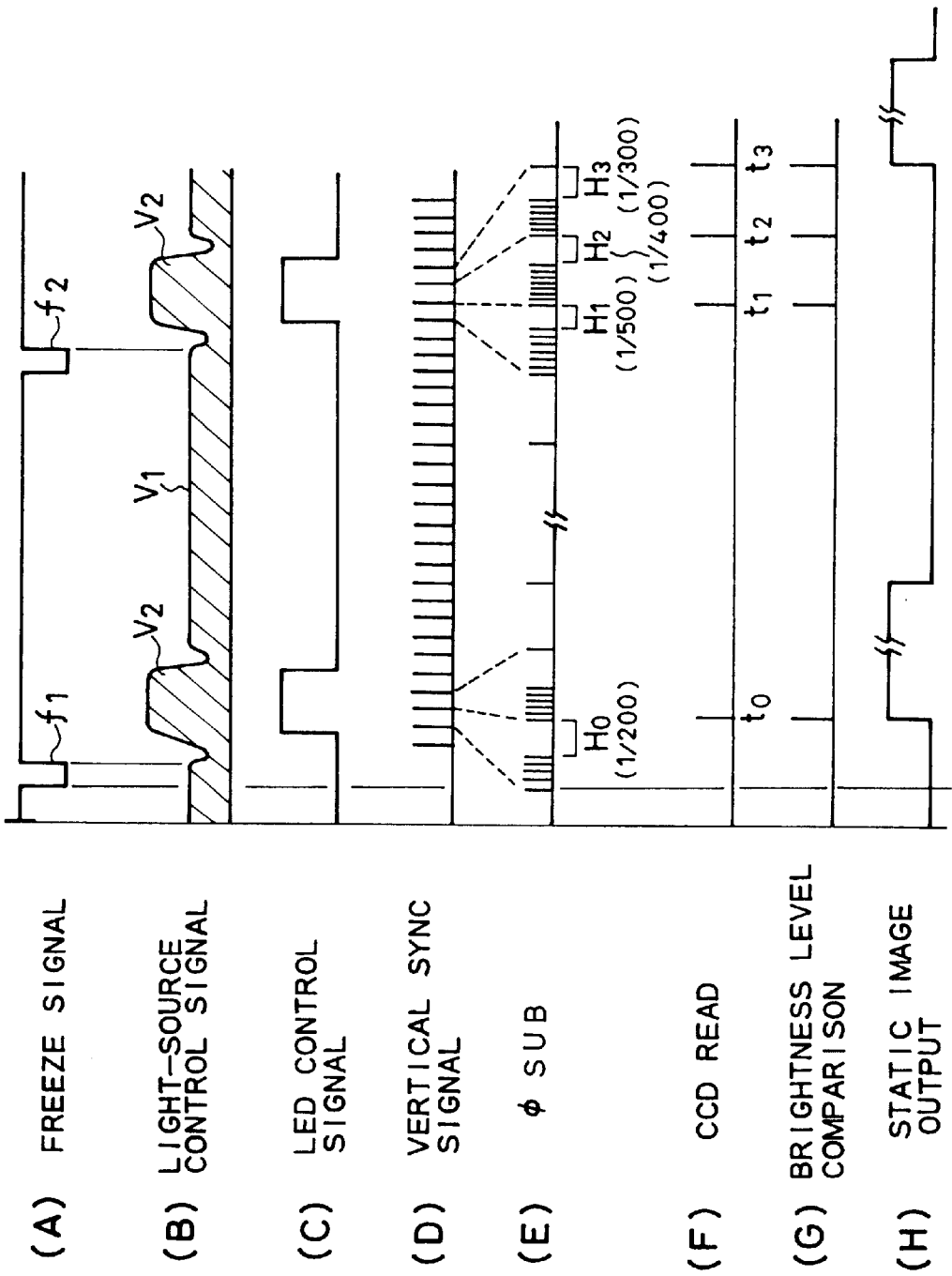
FIG. 2 is a flow chart showing operations of the embodiment in FIG. 1.

The above embodiment comprises the above configuration and its functions will be described below by referring to FIG. 2. The light of the light-source lamp 41 in FIG. 1 is emitted from the front end of the electronic endoscope 10 through the light guide 38 and thereby, the inside of an observation object is picked up by the CCD 16 through objective optical systems 13 and 14. In the case of this embodiment, when the variable-power switch 21 or freeze button 25 of the operating section of the electronic endoscope 10 is not pressed, shutter speed control is not executed by the electronic shutter circuit 30 but charges stored for approx ⅟60 sec are read. Then, the read signal is processed as a video signal and thereby, a color difference signal C and a brightness signal Y are output from an encoder 48. Thus, an image of the inside of an observation object is displayed on a monitor.

On the other hand, when the variable-power switch 21 is operated, the movable lens 14 moves forward from the standard position through the lens moving mechanism section 18 by rotating the linear transmission member 19 by the variable-power motor 20 and an image is enlarged. As the same time, the optical variable-power position of the movable lens 14 detected by the encoder 23 is supplied to the variable-power motor 20 and also supplied to the CPU 28 as current variable-power position information.

Then, when the freeze switch 25 is pressed, the freeze signal $f_1$ shown in FIG. 2A is input to the CPU 28 and the CPU 28 first supplies a stroboscopic-light-emitting command to the stroboscopic light emission circuit 42. Then, the stroboscopic light emission circuit 42 supplies a voltage $V_2$ having a waveform instantaneously rising for a short period compared to a signal voltage $V_1$ when a dynamic image is formed to the lamp 41 and thereby, stroboscopic light is output for several vertical-operation periods.

In the case of this embodiment, when the freeze button 25 is pressed, the electronic shutter of the CCD 16 is simultaneously accelerated. That is, the CPU 28 outputs an acceleration command for forming a static image to the electronic shutter circuit 30 and the electronic shutter circuit 30 changes a shutter speed, for example, from 1/60 sec to 1/200 sec. FIG. 2D shows the timing of a vertical sync signal and FIG. 2E shows an output state of a sweep-out pulse φSUB supplied to the CCD 16 in an enlarged view of the vertical sync signal in FIG. 2D. A charge storing time $H_0$ after the output of the sweep-out pulse φSUB is stopped such as 1/200 sec serves as a shutter speed.

Moreover, as shown in FIG. 2F, a video signal is read from the CCD 16 at a timing $t_0$ when the shutter speed $H_0$ is completed and the brightness level of the video signal is determined at a timing almost same as the timing to as shown in FIG. 2G. That is, the CPU 28 receives, for example, a brightness signal output from the signal processing circuit 34 in FIG. 1, and it is determined by the CPU 28 whether the brightness of an image is preferable. When the brightness meets a predetermined reference value, a static image obtained at the shutter speed $H_0$ is output as shown in FIG. 2H.

However, when a freeze signal $f_2$ is output but the brightness level of a video signal obtained at a shutter speed $H_1$ (e.g. 1/500 sec) shown in FIG. 2F does not meet a predetermined reference value, the CPU 28 lowers a shutter speed to $H_2$ (e.g. 1/400 sec) to perform the same brightness-level determination. Then, when the brightness level does not meet the reference value even at $H_2$, the CPU 28 sets a lower shutter speed $H_3$ (e.g. 1/300 sec). In this case, as shown in FIG. 2H, a static image obtained at the shutter speed $H_3$ meeting a predetermined brightness is output.

In the case of this embodiment, the above stroboscopic light emission and acceleration of electronic shutter speed are performed independently of whether variable power is operated. This is particularly effective when variable-power operation is performed by the variable-power switch 21. That is, when enlarging an observation object, blurring is emphasized and a state that cannot be seen as a static image may appear. Therefore, by increasing the quantity of light through stroboscopic light emission and accelerating a shutter speed by the time equivalent to the increase of the quantity of light, influence of blurring decreases and it is possible to obtain an enlarged static image having a high quality.

Moreover, in the case of this embodiment, even when stroboscopic light is not emitted while a dynamic image is formed, a shutter speed is accelerated under variable-power operation. That is, the CPU 28 outputs an acceleration command to the electronic shutter circuit 30 under variable-power operation and the circuit 30 is controlled so that a shutter speed rises as an enlargement rate increases, for example. Therefore, influence of blurring is decreased due to acceleration of a shutter speed even for a dynamic image under variable-power operation.

In this case, when the freeze button 25 is pressed, a shutter speed which further rises only by a predetermined time is set on the basis of the shutter speed set immediately before switching operation by the electronic shutter circuit 30 and simultaneously, stroboscopic light is emitted by the stroboscopic light emission circuit 42. Thereby, it is possible to further improve the quality of a static image.

In the case of the above embodiment, emission of stroboscopic light and acceleration of shutter speed are performed while a static image is formed even when variable-power operation is not performed. However, it is possible to perform emission of stroboscopic light and acceleration of shutter speed only under variable-power operation, that is, only under enlargement in which image blurring becomes remarkable.

Figure 3:
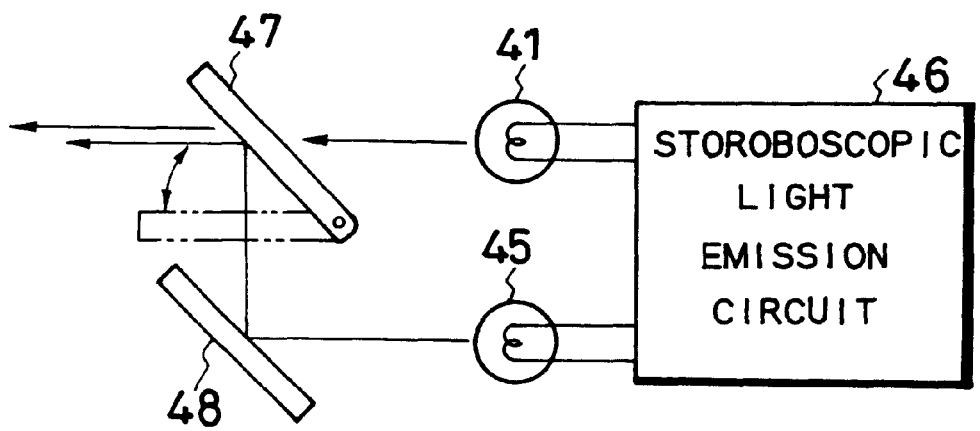
FIG. 3 is an illustration showing another configuration for stroboscopic light emission in an embodiment.

FIG. 3 shows another configuration for stroboscopic light emission, which executes stroboscopic light emission by additionally using a spare light-source lamp. In FIG. 3, a lamp 45 for stroboscopic light emission is used separately from the lamp 41 and a stroboscopic light emission circuit 46 for turning on/off these lamps 41 and 45 is set. Then, a rotary half mirror 47 is set to the front of the lamp 41 and a fixed mirror 48 is set to the front of the other lamp 45.

According to the configuration in FIG. 3, only the light-source lamp 41 is turned on while a dynamic image is formed. However, when the freeze button 25 is pressed, the lamp 45 is turned on together with the lamp 41 by the stroboscopic light emission circuit 46 and simultaneously, the half mirror 47 is driven up to a position of 45° and set to the front of the lamp 41. As a result, added light of the lamps 41 and 45 is emitted as stroboscopic light and thereby, a static image of an observation object is formed by illumination light brighter than the light for a dynamic image.

Figure 4:
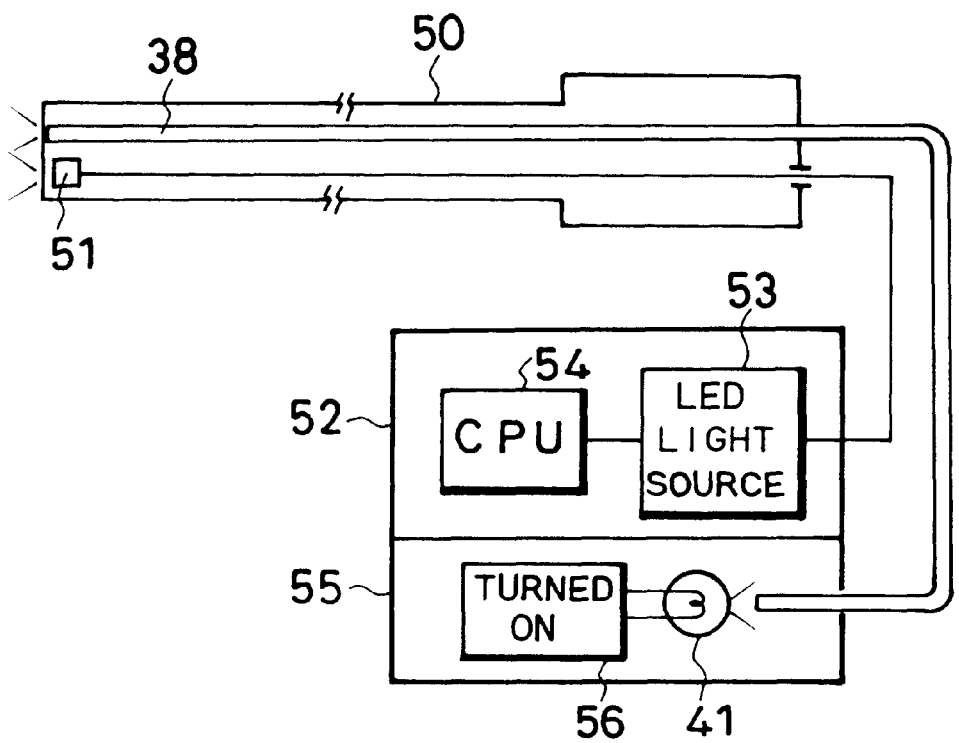
FIG. 4 is an illustration showing still another configuration for stroboscopic light emission in an embodiment.

FIG. 4 shows still another configuration for stroboscopic light emission, in which an LED (light-emitting diode) added to emit stroboscopic light is set to the front end. In FIG. 4, an LED 51 is set to the front end of an electronic endoscope 50, an LED power-supply circuit 53 and a CPU 54 for driving the circuit 53 are set in a processor 52 to which the electronic endoscope 50 is connected, and a turn-on circuit 56 for turning on the light-source lamp 41 is set to a light-source unit 55 to which the light guide 38 is connected.

According to the configuration in FIG. 4, only the light-source lamp 41 is turned on by the turn-on circuit 56 while a dynamic image is formed. However, when the freeze button 25 is pressed, the CPU 54 turns on the LED power-supply circuit 53 to turn on the LED 51 at the front end. As a result, the added light of the lamp 41 and LED 51 is emitted as stroboscopic light and thereby, a static image of an observation object is formed by illumination light brighter than the light for a dynamic image.

As described above, the above embodiment makes it possible to prevent image blurring which becomes remarkable for an enlarged image in particular and form a preferable static image free from exposure deficiency.

What is claimed is:

1. An electronic endoscope apparatus, comprising:
    a solid-state image pickup device for picking up an observation object;
    an electronic shutter circuit comprising a timing generator for controlling a charge storing time of the solid-state image pickup device by adjusting a sweep-out time of the image pickup device using a sweep-out pulse;
    a stroboscopic light emission section for instantaneously emitting the stroboscopic light stronger than an illumination light emitted to an observation object under normal observation;

an optical variable-power mechanism capable of optically enlarging an observation image by an objective optical system; and a control circuit for setting a shutter speed faster than that for a dynamic image by the electronic shutter circuit when a static image is selected in accordance with a freeze signal while the optical variable-power mechanism is operated and controlling the stroboscopic light emission section so as to emit the stroboscopic light.

2. The electronic endoscope apparatus according to claim 1, wherein the stroboscopic light emission section is provided with a static-image-forming light source in addition to a light source used to form a dynamic image and the control circuit additionally turns on the static-image-forming light source when receiving a freeze signal.

3. The electronic endoscope apparatus according to claim 2, wherein an LED is set to the front end of the electronic endoscope as the static-image-forming light source.

* * * * *